(12) United States Patent
Bromme

(10) Patent No.: US 7,799,326 B2
(45) Date of Patent: Sep. 21, 2010

(54) METHODS AND COMPOSITIONS FOR CATHESPIN K COMPLEX-MEDIATED DISORDERS

(75) Inventor: Dieter Bromme, Tenafly, NJ (US)

(73) Assignee: Mount Sinai School of Medicine, New York, NY (US)

( * ) Notice: Subject to any disclaimer, the term of this patent is extended or adjusted under 35 U.S.C. 154(b) by 728 days.

(21) Appl. No.: 10/490,759

(22) PCT Filed: Sep. 24, 2002

(86) PCT No.: PCT/US02/30198

§ 371 (c)(1),
(2), (4) Date: Jul. 8, 2004

(87) PCT Pub. No.: WO03/041635

PCT Pub. Date: May 22, 2003

(65) Prior Publication Data

US 2004/0241157 A1    Dec. 2, 2004

Related U.S. Application Data

(60) Provisional application No. 60/324,445, filed on Sep. 24, 2001.

(51) Int. Cl.
*A61K 38/43* (2006.01)
*A61K 38/48* (2006.01)
*C12N 9/50* (2006.01)
*C12N 9/64* (2006.01)

(52) U.S. Cl. ............ 424/94.63; 424/146.1; 435/226; 530/388.26

(58) Field of Classification Search ............ None
See application file for complete search history.

(56) References Cited

U.S. PATENT DOCUMENTS

| 5,830,850 | A * | 11/1998 | Gelb et al. ............ 514/2 |
| 5,948,669 | A | 9/1999 | Feild et al. |
| 5,948,692 | A | 9/1999 | Miyauti et al. |
| 6,218,433 | B1 | 4/2001 | Ameys |
| 6,274,336 | B1 | 8/2001 | Abdel-Meguid et al. |

OTHER PUBLICATIONS

Accession # NP_001029607 from NCBI GenBank.*
Accession # AAA29137 from NCBI GenBank.*
Osteoporosis from Merck Manual, pp. 1-6. Accessed Jun. 11, 2009.*
Skin aging from Merck Manual, pp. 1-2. Accessed Jun. 11, 2009.*
Paget's Disease from Merck Manual, pp. 1-4. Accessed Jun. 11, 2009.*
Rheumatoid Arthritis from Merck Manual, pp. 1-11. Accessed Jun. 11, 2009.*
Gelb et al. (2001) Science 273:1236-1238.
Hou et al. (1999) J. Clin. Invest. 103:731-738.
Kafienah et al. (1998) Biochem J. 331:727-732.
Li (2000) Biochemistry 39:529-536.
Shi et al. (1995) FEBS Lett 357:129-134.

* cited by examiner

*Primary Examiner*—Julie Ha

(57) ABSTRACT

Methods and compositions for the amelioration of symptoms mediated by the collagenolytic activity of cathepsin K complex are provided. Methods of specifically modulating the collagenolytic activity of cathepsin K without substantial interference in other biologically-relevant activities of cathepsin K are further provided.

9 Claims, 1 Drawing Sheet

METHODS AND COMPOSITIONS FOR CATHESPIN K COMPLEX-MEDIATED DISORDERS

STATEMENT OF RELATED APPLICATIONS

This application claims priority under 35 USC §119(e) to U.S. Ser. No. 60/324,445 filed Sep. 24, 2001, the contents of which application are herein specifically incorporated by reference in its entirety.

BACKGROUND OF THE INVENTION

1. Field of the Invention

The present invention relates to therapeutic methods, screening methods, and composition comprising a cathepsin K complex exhibiting specific collagenolytic activity.

2. Related Art

Cathepsin K is a cysteine protease of the papain family that is highly expressed in bone and cartilage-degrading cells such as osteoclasts, giant multinucleated cells and synovial fibroblasts. It is estimated that cathepsin K constitutes approximately 98% of all cysteine protease activities expressed in osteoclasts, and thus may be primarily responsible for most of the proteolytic activity in bone resorption.

Cathepsin K has a unique collagenolytic activity that allows the efficient degradation of native collagen fibers. Since type I collagen constitutes more than 90% of the organic bone matrix and type II collagen is the major protein in cartilage, collagen degradation is thought to be the major biologically-relevant activity of cathepsin K.

Cathepsin K has been identified as a novel pharmaceutical target for the design of anti-resorptive drugs. The main indications for the use of cathepsin inhibitors are osteoporosis, Paget's disease, rheumatoid arthritis, and possibly osteoarthritis. The common feature of these diseases is the excessive and irreversible degradation of extracellular bone and cartilage matrix.

Cathepsin K is expressed in a variety of additional cell types such as macrophages, and various epithelial cells with potential functions in antigen processing, thyroglobulin processing and other functions yet to be determined. Thus, active-site directed inhibitors against cathepsin K which result in inhibition of excessive extracellular matrix degradation, will also inhibit many other biologically important cathepsin K activities. Thus, inhibition or disruption of non-deleterious cathepsin K activities may result in undesirable and deleterious effects.

It would be useful to specifically inhibit a single cathepsin K activity, for example, collagen degradation, without inhibiting other biologically-relevant activity.

BRIEF SUMMARY OF THE INVENTION

The present invention is based, in part, on the discovery that the collagenolytic activity of cathepsin K requires the formation of an oligomeric cathepsin K complex from monomeric (free) cathepsin K and specific glycosaminoglycans. Thus, the high specificity of cathepsin K for triple-helical collagen is a property of the complexed protein formed from specific component glycosaminoglycans, and is not exhibited by the free protein or a complex formed from non-productive glycosaminoglycans. Accordingly, the present invention provides methods for specifically modulating the collagenolytic activity of cathepsin K without inhibiting other biologically-relevant activities of cathepsin K.

In a first aspect, the invention provides a substantially pure collagenolytically active cathepsin K oligomeric complex that degrades type I and type II collagen with a high specificity relative to that of free cathepsin K, which has no collagenolytic activity. The cathepsin K complex of the invention may comprise the native mature cathepsin K peptide, or other cathepsin K molecules, such as analogs, variants, and fragments thereof, complexed with one or more specific glycosaminoglycans, such that the complex exhibits increased collagenolytic activity over monomeric (free) cathepsin K.

In one embodiment, a collagenolytically active cathepsin K complex of the invention comprises 2-10 cathepsin K peptides and 2-10 glycosaminoglycan molecules. In a more specific embodiment, a collagenolytically active cathepsin K complex of the invention comprises 5 cathepsin K peptides and 5 glycosaminoglycan molecules. In a more specific embodiment, the glycosaminoglycan molecule is chondroitin sulfate (CS).

The cathepsin K complex of the invention can also be used to produce antibodies that are immunoreactive or bind epitopes of the collagenolytically active cathepsin K complex. Accordingly, in a second aspect, the invention features antibodies to a cathepsin K complex of the invention. The antibodies of the invention include polyclonal antibodies which consist of pooled monoclonal antibodies with different epitopic specificities, as well as distinct monoclonal antibody preparations. Monoclonal antibodies are made from antigen-containing fragments of the cathepsin K polypeptide by methods known in the art (see, for example, Kohler et al. (1975) Nature 256:495).

The cathepsin K complexes of the invention are useful to screen reagents capable of specifically modulating the collagenolytic activity of a cathepsin K complex without effecting other biological activities of the free peptide. Accordingly, in a third aspect, the invention features methods for identifying a reagent which modulates collagenolytically active cathepsin K complex activity, by incubating a cathepsin K complex with the test reagent and measuring the effect of the test reagent on cathepsin K complex activity. Specific modulation embodiments include upregulation, e.g., increasing or enhancing the collagenolytic activity of a cathepsin K complex, and downregulation, e.g., inhibiting or decreasing the collagenolytic activity of a cathepsin K complex.

The cathepsin K complexes of the invention are also useful to screen reagents capable of modulating the formation of a collagenolytically active cathepsin K complex. Accordingly, in a fourth aspect, the invention features methods for identifying a reagent which modulates collagenolytically active cathepsin K complex formation, by incubating free complex components, e.g., free cathepsin K and glycosaminoglycans capable of forming a collagenolytically active (productive) complex with cathepsin K, with the test reagent and measuring the effect of the test reagent on cathepsin K complex formation. Reagents thus identified may modulate cathepsin K complex formation by increasing or enhancing complex formation, or inhibiting, decreasing, or blocking formation of a collagenolytically active complex. Reagents may also modulate cathepsin K complex formation by favoring formation of a non-productive complex (i.e.,non-collagenolytic) over formation of a productive complex.

In a fifth aspect, the invention further features a method of treating a cathepsin K complex-mediated disorder by administering to a subject in need thereof an effective dose of a therapeutic reagent that alters or effects cathepsin K complex activity. In one embodiment, a disorder results from excessive cathepsin K complex activity and the therapeutic agent specifically inhibits the collagenolytic activity of a cathepsin K complex. In another embodiment, a disorder results from excessive cathepsin K complex activity and the therapeutic agent specifically inhibits formation of a collagenolytically active (productive) cathepsin K complex.

In one embodiment, a disorder results from insufficient cathepsin K complex activity, and the therapeutic agent specifically enhances the collagenolytic activity of a cathepsin K complex. In a related embodiment, a disorder results from insufficient cathepsin K complex activity and the therapeutic agent specifically increases formation of a collagenolytically active cathepsin K complex.

The materials of the invention are ideally suited for the preparation of a kit for the detection of the level or activity of cathepsin K complex. Accordingly, the invention features a kit comprising an antibody that binds cathepsin K complex, and suitable buffers. The probe or monoclonal antibody can be labeled to detect binding to collagenolytic cathepsin K complex. In a preferred embodiment, the kit features a labeled antibody to cathepsin K complex.

Other objects and advantages will become apparent from a review of the ensuing detailed description taken in conjunction with the following illustrative drawing.

DETAILED DESCRIPTION OF THE INVENTION

Figure 1:
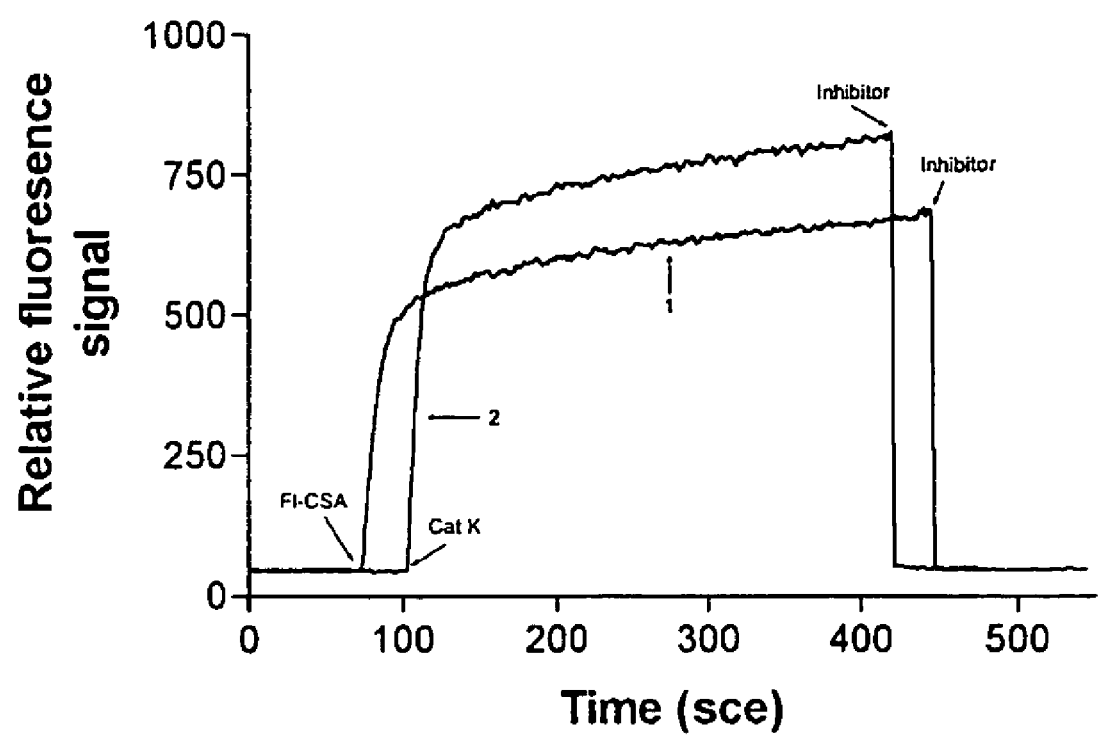
FIG. 1: Detection of CSA/Cat K complex formation and inhibition. CSA/Cat K complex formation and dissociation were tested in 100 mM sodium acetate buffer, pH 5.5 including 2 mM EDTA/DTT in a cuvette assay using a Perkin-Elmer fluorimeter at excitation and emission wavelengths of 300 nm and 604 nm, respectively. Curve 1: 120 nM Cat K, then 0.6 µg/ml FL-CSA, and then 3 µg/ml dextran sulfate; Curve 2:,0.6 µg/ml FL-CSA, then 120 nM Cat K, and then 3 µg/ml dextran sulfate.

Before the present collagenolytically active cathepsin K complex molecules, assay methodology, and treatment methodology are described, it is to be understood that this invention is not limited to particular assay methods, collagenolytically active cathepsin K complexes, or test compounds and experimental conditions described, as such methods and compounds may vary. It is also to be understood that the terminology used herein is for the purpose of describing particular embodiments only, and is not intended to be limiting, since the scope of the present invention will be limited only the appended claims.

As used in this specification and the appended claims, the singular forms "a", "an", and "the" include plural references unless the context clearly dictates otherwise. Thus for example, references to "a collagenolytically active cathepsin K complex" includes mixtures of such complexes, reference to "the formulation" or "the method" includes one or more formulations, methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to describe the methods and/or materials in connection with which the publications are cited.

Definitions

By the phrase "collagenolytically active cathepsin K complex" is meant a complex comprising a plurality of cathepsin K peptides in association with a plurality of glycosaminoglycan molecules which exhibits a specific collagenolytic activity relative to free cathepsin K. "Specific collagenolytic activity" means an ability to hydrolyze triple-helical collagen, e.g., type I or type II collagen.

A collagenolytically active cathepsin K complex may comprise a mature cathepsin K peptide, a pro-peptide, pre-propeptide, analog, homolog, derivative, or variant thereof. The cathepsin K complex may include any form of cathepsin K capable of forming an oligomeric complex with specific collagenolytic activity, including, mature, pre- or pro-cathepsin K (see, for example, Shi et al. (1995) FEBS Lett. 357:129-134, herein specifically incorporated by reference in its entirety).

"Cathepsin K homolog" refers to a polypeptide that comprises an amino acid sequence similar to that of cathepsin K, but does not necessarily possess a similar or identical function as the cathepsin K. "Cathepsin K ortholog" refers to a non-human polypeptide that (i) comprises an amino acid sequence similar to that of cathepsin K, and (ii) possesses a similar or identical function to that of cathepsin K. "Cathepsin K-related polypeptide" refers to a cathepsin K homolog, a cathepsin K analog, a cathepsin K ortholog, or any combination thereof. "Cathepsin K derivative" refers to a polypeptide that comprises an amino acid sequence of a cathepsin K polypeptide which has been altered by the introduction of amino acid residue substitutions, deletions or additions. The derivative polypeptide possesses a similar or identical function as the cathepsin K polypeptide.

"Native" or "naturally occurring" cathepsin K complex means a collagenolytically active cathepsin K complex found in nature, for example, in a mammal.

"Fragment" refers to a peptide or polypeptide comprising an amino acid sequence of at least 5 amino acid residues (preferably, at least 10 amino acid residues, at least 15 amino acid residues, at least 20 amino acid residues, at least 25 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, at least 150 amino acid residues, at least 175 amino acid residues, at least 200 amino acid residues, or at least 250 amino acid residues) of the amino acid sequence of a cathepsin K polypeptide.

The term "substantially pure," when referring to a polypeptide, means a polypeptide that is at least 60%, by weight, free from the proteins and naturally-occurring organic molecules with which it is naturally associated. A substantially pure cathepsin K protein complex is at least 75%, more preferably at least 90%, and most preferably at least 99%, by weight, human cathepsin K protein complex. A substantially pure human cathepsin K protein complex can be obtained, for example, by extraction from a natural source; by expression of a recombinant nucleic acid encoding a human cathepsin K protein complex, or by chemically synthesizing the protein and adding the complexing agents. Purity can be measured by any appropriate method, e.g., column chromatography, polyacrylamide gel electrophoresis, or HPLC analysis.

"Cathepsin K complex-associated disorders" or "cathepsin K complex-mediated diseases" and such, mean disorders and diseases which result from excessive bone and cartilage erosion resulting from the collagenolytic activity of the cathepsin K complex, or from insufficient collagenolytic activity of the cathepsin K complex.

The term "modulation cathepsin K complex activity" means modulation (e.g., up or down regulation, enhancement or inhibition of activity, etc.) specifically of the collagenolytic activity of the cathepsin K complex of the invention, e.g., the triple-helical collagen hydrolyzing activity of the complex, and includes inhibitory or stimulatory effects. In one embodiment, the invention includes methods for screening reagents that inhibit or prevent cathepsin K complex formation, and thus decrease or prevent collagenolytic activity without effecting other biological activities of the free cathepsin K molecule. Such reagents are useful for the treatment or prevention of cathepsin K protein complex-mediated disorders, for example, osteoporosis, Paget's disease, and rheumatoid arthritis. The common feature of these diseases is the excessive and irreversible degradation of extracellular bone and cartilage matrix.

As used herein, the term "therapeutic reagent" means any compound or molecule that achieves the desired effect on a cathepsin K complex-mediated disorder when administered to a subject in need thereof. A therapeutic reagent that "inhibits cathepsin K complex activity" interferes with cathepsin K complex activity or cathepsin K complex formation. For example, a therapeutic reagent can inhibit collagenase breakdown by inhibiting the collagenolytic activity of cathepsin K complex, or by inhibiting the formation of an active cathepsin K complex. A therapeutic reagent that "enhances cathepsin K complex activity" increases the collagenolytic activity of the cathepsin K complex or promotes formation of the cathepsin K complex. A "therapeutically effective amount" is an amount of a reagent sufficient to decrease or prevent the symptoms associated with the cathepsin K protein complex-mediated disorder.

General Aspects of the Invention

The present invention described in detail below provides methods for the treatment and/or amelioration of disorders mediated specifically by the collagenolytic activity of cathepsin K oligomeric complexes.

The instant invention is based, in part, on the discovery that the unique collagenolytic activity of cathepsin K requires the formation of an oligomeric cathepsin K complex from monomeric (free) cathepsin K molecules and specific glycosaminoglycans. Monomeric cathepsin K has only a minimal (if any) ability to degrade triple-helical collagens, but has a high activity towards various non-collagenolytic substrates, e.g., gelatin and synthetic peptide substrates. Cathepsin K peptide is able to complex with various glycosaminoglycans, but not all the complexes exhibit collagenolytic activity. The most potent glycosaminoglycans involved in formation of a productive collagenolytically active complex are bone-and cartilage-resident chondroitin and keratan sulfates.

This discovery makes possible a completely new strategy to selectively inhibit or enhance the pharmaceutically relevant collagenolytic activity of cathepsin K towards triple-helical collagens without interfering with other activities of the enzyme. Compounds interfering with the formation of functionally active collagenolytic cathepsin K complex will lead to a selective loss of the cathepsin K complex collagenase activity, while retaining the activity of free cathepsin K towards most non-collagen substrates. Therefore, the design of selective complex formation inhibitors is expected to avoid potentially negative side effects of classical site-directed inhibitors, as well as avoid difficulties in the design of highly specific inhibitors due to redundancy of closely related cathepsins with similar active sites.

Collagenolytically active cathepsin K is a complex comprised of five cathepsin K peptides and five chondroitin sulfate (CS) molecules, with a composite molecular weight of 275 kD. Electron microscopy analysis revealed a pentameric ring structure of 120-130 Å in diameter with a central pore of 25-30 Å sufficient to accommodate helical collagen trimers with a diameter of 15 Å. As is described more fully below, inhibition of complex formation led to the loss of collagenolytic activity but did not affect the activity of the enzyme towards gelatin and synthetic substrates.

Screening Assays

The invention provides methods for identifying agents (e.g., chemical compounds, carbohydrates, proteins, peptides, or nucleotides) that have a stimulatory or inhibitory effect on the formation or activity of a collagenolytically active cathepsin K complex. The invention also provides methods of identifying agents, candidate compounds or test compounds that specifically bind to a cathepsin K complex. Examples of agents, candidate compounds or test compounds include, but are not limited to, nucleic acids (e.g., DNA and RNA), carbohydrates, lipids, proteins, peptides, peptidomimetics, small molecules and other drugs. Agents can be obtained using any of the numerous suitable approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, 1997, Anticancer Drug Des. 12:145; U.S. Pat. No. 5,738,996; and U.S. Pat. No. 5,807,683, each of which is incorporated herein in its entirety by reference).

In one embodiment, agents that interact with (i.e., bind to) a cathepsin K complex comprising cathepsin K polypeptide, a cathepsin K peptide fragment (e.g. a functionally active fragment), or a cathepsin K-related polypeptide, are identified in a cell-based assay system. In accordance with this embodiment, cells expressing a cathepsin K complex comprising a cathepsin K peptide or polypeptide, a fragment thereof, or a cathepsin K-related polypeptide, are contacted with a candidate compound or a control compound and the ability of the candidate compound to interact with the cathepsin K complex is determined. If desired, this assay may be used to screen a plurality (e.g., a library) of candidate compounds. The cell, for example, can be of prokaryotic origin (e.g., *E. coli*) or eukaryotic origin (e.g., yeast or mammalian). Further, the cells can express the cathepsin K peptide or polypeptide, fragment, or related polypeptide thereof, endogenously or be genetically engineered to express the cathepsin K peptide or polypeptide, fragment, or related polypeptide thereof. In some embodiments, the cathepsin K peptide or polypeptide, fragment, or related polypeptide thereof or the candidate compound is labeled, for example with a radioactive label (such as $^{32}$P, $^{35}$S or $^{125}$I or a fluorescent label (such as fluorescein isothiocyanate, rhodamine, phycoerythrin, phycocyanin, allophycocyanin, o-phthaldehyde or fluorescamine) to enable detection of an interaction between a cathepsin K complex and a candidate compound. The ability of the candidate compound to interact directly or indirectly with the cathepsin K complex can be determined by methods known to those of skill in the art. For example, the interaction can be determined by flow cytometry, a scintillation assay, immunoprecipitation or western blot analysis.

In another embodiment, agents interact with (i.e., bind to) a cathepsin K complex in a cell-free assay system. In accordance with this embodiment, a cathepsin K complex is contacted with a candidate compound or a control compound and the ability of the candidate compound to interact with the cathepsin K complex is determined. If desired, this assay may be used to screen a plurality (e.g. a library) of candidate compounds. In specific embodiments, the cathepsin K complex is first immobilized, by, for example, contacting the cathepsin K complex with an immobilized antibody which specifically recognizes and binds it, or by contacting a purified preparation of the cathepsin K complex with a surface designed to bind proteins. The cathepsin K complex may be partially or completely purified (e.g., partially or completely free of other polypeptides) or part of a cell lysate. The ability of the candidate compound to interact with the cathepsin K complex can be can be determined by methods known to those of skill in the art.

In another embodiment, a cell-based assay system is used to identify agents that bind to or modulate the activity of the cathepsin K complex, or a biologically active portion thereof, which is responsible for the degradation of triple-helical collagen. In a primary screen, a plurality (e.g., a library) of compounds are contacted with cells that naturally or recombinantly express components which form an enzymatically active collagenolytic cathepsin K complex in order to identify compounds that modulate the formation of the complex molecule. The ability of the candidate compound to modulate the formation of the cathepsin K complex can be determined by methods known to those of skill in the art, including without limitation, flow cytometry, a scintillation assay, immunoprecipitation and western blot analysis.

In another embodiment, agents that competitively interact with (i.e., bind to) a cathepsin K complex are identified in a competitive binding assay. In accordance with this embodiment, cells expressing components of the cathepsin K complex able to form the collagenolytically active complex are contacted with a candidate compound and a compound known to interact with the cathepsin K complex or prevent the formation of an active cathepsin K complex; the ability of the candidate compound to competitively interact with the cathepsin K complex or to competitively prevent formation of the cathepsin K complex is then determined. Alternatively, agents that competitively interact with (i.e., bind to) a cathepsin K complex or competitively prevent the formation of an collagenolytically active cathepsin K complex are identified in a cell-free assay system by contacting the cathepsin K complex or components able to form an active cathepsin K complex with a candidate compound and a compound known to interact with or prevent the formation of the cathepsin K complex. As stated above, the ability of the candidate compound to interact with a cathepsin K complex or prevent the formation of an active cathepsin K complex can be determined by methods known to those of skill in the art. These assays, whether cell-based or cell-free, can be used to screen a plurality (e.g., a library) of candidate compounds.

In another embodiment, agents that modulate (i.e., up-regulate or down-regulate) the formation of an collagenolytic cathepsin K complex or the collagenolytic activity of an existing cathepsin K complex are identified by contacting cells (e.g., cells of prokaryotic origin or eukaryotic origin) expressing the components capable of forming an enzymatically active collagenolytic cathepsin K complex with a candidate compound or a control compound (e.g. phosphate buffered saline (PBS)) and determining the formation or activity of the cathepsin K complex. The level of active complex formation or complex activity in the presence of the candidate compound is compared to the level of formation or activity in the absence of the candidate compound (e.g., in the presence of a control compound). The candidate compound can then be identified as a modulator of the expression of the cathepsin K complex based on this comparison. For example, when presence of an enzymatically active cathepsin K complex is significantly greater in the presence of the candidate compound than in its absence, the candidate compound is identified as a stimulator of complex formation and/or an enhancer of complex activity. Alternatively, when presence of an enzymatically active cathepsin K complex is significantly less in the presence of the candidate compound than in its absence, the candidate compound is identified as an inhibitor of complex formation and/or inhibitor of complex activity.

In another embodiment, agents that modulate the activity of an enzymatically active collagenolytic cathepsin K complex are identified by contacting a preparation containing the complex, or cells (e.g., prokaryotic or eukaryotic cells) forming an enzymatically active collagenolytic cathepsin K complex with a test compound or a control compound and determining the ability of the test compound to modulate (e.g., stimulate or inhibit) the activity of the cathepsin K complex. The activity of the cathepsin K complex can be assessed in a number of ways, including by, e.g., determining hydrolysis of triple-helical collagen.

In another embodiment, agents that modulate (i.e., up-regulate or down-regulate) the formation, activity or both, of a cathepsin K complex are identified in an animal model. Examples of suitable animals include, but are not limited to, mice, rats, rabbits, monkeys, guinea pigs, dogs and cats. Preferably, the animal used represents a model of a cathepsin K complex-associated disorder, e.g., osteoporosis.

In accordance with this embodiment, the test compound or a control compound is administered (e.g., orally, rectally or parenterally such as intraperitoneally or intravenously) to a suitable animal and the effect on the formation, activity or both formation and activity of the cathepsin K complex is determined, or the effect on a cathepsin K complex target cell is determined. Changes in the activity of a cathepsin K complex can be assessed by any suitable method described above, based on the present description.

This invention further provides novel agents identified by the above-described screening assays and uses thereof for treatments as described herein.

Therapeutic Uses of the Invention

The invention provides for treatment or prevention of various diseases and disorders by administration of a therapeutic agent. Such agents include but are not limited to: agents which promote or prevent formation of the enzymatically active collagenolytic cathepsin K complex, agents which modulate the activity of enzymatically active collagenolytic cathepsin K complex, agents able to act as antagonists or agonists of the enzymatically active collagenolytic cathepsin K complex, and the enzymatically active collagenolytic cathepsin K complex itself, and related analogs, derivatives, and fragments thereof; antibodies to the foregoing.

In one embodiment wherein inhibition of the enzymatically active collagenolytic cathepsin K complex is desirable, one or more antibodies each specifically binding to the cathepsin K complex are administered alone or in combination with one or more additional therapeutic compounds or treatments. Preferably, a biological product such as an antibody is allogeneic to the subject to which it is administered. In a preferred embodiment, a human cathepsin K complex is administered to a human subject for therapy (e.g. to ameliorate symptoms or to retard onset or progression) or prophylaxis.

Assays For Therapeutic or Prophylactic Compounds

The present invention also provides assays for use in discovery of pharmaceutical products in order to identify or verify the efficacy of compounds for treatment or prevention of cathepsin K complex-mediated diseases. In one embodiment, agents can be assayed for their ability to reduce bone resorption activity in a subject suffering from osteoporosis towards levels found in subjects free from any osteoporosis diseases or to produce similar changes in experimental animal models of osteoporosis. Compounds able to reduce the collagenolytic activity of cathepsin K complex levels in a subject suffering from a disorder related to excessive bone resorption in a subject towards healthy levels found in subjects free from osteoporosis, or able to produce similar changes in experimental animal models of osteoporosis can be used as lead compounds for further drug discovery, or used therapeutically.

In various embodiments, in vitro assays can be carried out with cells representative of cell types involved in a subject's disorder, to determine if a compound has a desired effect upon such cell types. In one embodiment, the cells are skin fibroblast cells, and the condition is undesirable wrinkling or aging due to age, smoking, sun-exposure, or other conditions.

Compounds for use in therapy can be tested in suitable animal model systems prior to testing in humans, including but not limited to rats, mice, chicken, cows, monkeys, rabbits, etc. For in vivo testing, prior to administration to humans, any animal model system known in the art may be used. In one embodiment, test compounds that modulate the formation or activity of enzymatically active collagenolytic cathepsin K complex are identified in non-human animals (e.g., mice, rats, monkeys, rabbits, and guinea pigs), preferably non-human animal models for cathepsin K complex-associated disorders. In accordance with this embodiment, a test compound or a control compound is administered to the animals, and the effect of the test compound on collagenolytic cathepsin K complex levels or activity is determined. A test compound that alters the level or activity of collagenolytic cathepsin K complex can be identified by comparing the level of the selected collagenolytic cathepsin K complex in an animal or group of animals treated with a test compound with the level of the collagenolytic cathepsin K complex in an animal or group of animals treated with a control compound.

In another embodiment, test compounds that modulate the activity of collagenolytic cathepsin K complex are identified in non-human animals (e.g., mice, rats, monkeys, rabbits, and guinea pigs), preferably non-human animal models for collagenolytic cathepsin K complex-mediated disorders. In accordance with this embodiment, a test compound or a control compound is administered to the animals, and the effect of a test compound on the activity of collagenolytic cathepsin K complex is determined. A test compound that alters the activity of collagenolytic cathepsin K complex can be identified by assaying animals treated with a control compound and animals treated with the test compound.

In yet another embodiment, test compounds that modulate the level or activity of collagenolytic cathepsin K complex are identified in human subjects having a cathepsin K complex-associated disorder. In accordance with this embodiment, a test compound or a control compound is administered to the human subject, and the effect of a test compound on collagenolytic cathepsin K complex activity, or bone resorption is determined by methods known in the art.

Therapeutic and Prophylactic Compositions and Their Use

The invention provides methods of treatment comprising administering to a subject an effective amount of an agent of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human. In one specific embodiment, a non-human mammal is the subject. In another specific embodiment, a human mammal is the subject.

Formulations and methods of administration that can be employed when the compound comprises a nucleic acid are described above; additional appropriate formulations and routes of administration are described below. Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:44294432), construction of a nucleic acid as part of a retroviral or other vector, etc. Methods of introduction can be enteral or parenteral and include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent. In a specific embodiment, it may be desirable to administer the pharmaceutical compositions of the invention locally to the area in need of treatment; any suitable method known to the art may be used.

The present invention also provides pharmaceutical compositions. Such compositions comprise a therapeutically effective amount of an agent, and a pharmaceutically acceptable carrier. In a particular embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides.

Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the subject. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The amount of the compound of the invention which will be effective in the treatment of cathepsin K complex-mediated disorders can be determined by standard clinical techniques based on the present description. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

Collagenolytically Active Cathepsin K Complex

The experiments described below demonstrate that bone and cartilage-resident glycosaminoglycans (GAGs) dramatically and specifically enhance the degradation of interstitial collagens of types I and II by cathepsin K. This effect is not seen with cathepsin L or matrix metalloproteinase I (Li (2000) Biochemistry 39:529-536). Hydrolysis of type I collagen by cathepsin K was shown to be dependent on the presence of chondroitin 4-sulfate (CSA), and specifically enhanced by increasing concentrations of CSA (Example 1).

Analysis of commercially available type I and II collagen samples revealed that contaminations with GAGs were responsible for the previously reported cathepsin K-mediated collagen degradation in the apparent absence of GAGs (Kafienah et al. (1998) Biochem J. 331:727-732; Garnero et al. (1998) J Biol Chem 273:32347-32352). Reduction of the GAG content in collagen samples by chondroitinase ABC treatment resulted in a significant reduction of the collagenolytic activity of cathepsin K towards type I collagen. This finding indicated that the presence of GAGs is essential for the collagen-degrading activity of cathepsin K.

Size-exclusion chromatography of purified recombinant cathepsin K and CSA mixtures revealed a proteolytically active, high molecular weight complex whose mass varied from 200-310 kD depending on the molecular mass fraction of CSA used (17 to 30 kD determined by dynamic light scattering) (Example 2).

When cathepsin K/CSA mixtures were eluted in the presence of 300 mM NaCl, cathepsin K activity corresponded to a peak of 25 kD identical to the elution peak obtained when cathepsin K was applied without CSA to the gel filtration column. This indicates that high salt concentration inhibits the formation of cathepsin K complexes. The absence or presence of NaCl had only a minor effect on the $k_{cat}/K_m$. value of cathepsin K on the hydrolysis of the fluorigenic dipeptide substrate, Z-LR-MCA, whereas the presence of 0.15% CSA doubled the specific activity (Table 1).

Complex formation was also detected in a electrophoretic mobility shift assay using [$^{125}$I]DCG-04 labeled cathepsin K in the presence of CSA. Cathepsin K/CSA complexes migrated to the anode whereas in the absence of CSA cathepsin K migrated to the cathode. In the presence of NaCl, the complex dissociated and cathepsin K migrated identically to the protease sample in the absence of CSA.

Using the mobility shift assay, the ratio between [$^{125}$I] DCG-04 labeled cathepsin K and CSA in the complex was determined. The plot of cathepsin K complex/CSA vs cathepsin K concentration resulted in a saturation curve reaching a plateau at a 1:1 ratio between cathepsin K and CSA.

The molecular mass of the cathepsin K/CSA complex in the presence of 30 kD CSA was determined by dynamic light scattering (DLS) and analytical ultracentrifugation. Measurements by DLS yielded in a molecular mass of 274±12 kD and the value obtained by ultracentrifugation was 284 kD Based on the molecular mass of the complex and the ratio of 1:1 between cathepsin K and CSA, the complex was determined to have the following stoichiometry: Cat $K_5$ $CSA_5$ with a molecular mass of 275 kD (using molecular masses for CSA, 29.8 kD and Cat K, 24.7 kD as determined by DLS). The hydrodynamic radius of the complex was determined by DLS to be 65.3±1.4 Å. Stoichiometry and hydrodynamic radius of the complex suggest a ring structure containing five cathepsin K molecules connected via five positively charged CSA molecules.

Electron microscopic examination supports the predicted 5-membered ring structure (not shown). The ring structure has a diameter of 120-130 Å with a central pore measuring 25-30 Å. This pore would allow access for linear triple helical collagen molecules with a diameter of 15 Å.

To determine if complex formation is required for the collagenolytic activity of cathepsin K, type I collagen was incubated with free cathepsin K or with cathepsin K/CSA complexes at 28 C and 37 C in the presence or absence of 300 mM NaCl. In the absence of NaCl, collagen is completely degraded by the protease/CSA complex whereas in the presence of NaCl neither cathepsin K alone nor in a mixture with CSA showed any degradation of the extracellular matrix protein. This suggested that triple helical type I collagen is resistant towards the activity of monomeric cathepsin K even at 37

C. The results showed that 300 mM NaCl inhibits oligomerization of cathepsin K in the presence of CSA. NaCl had no effect on the degradation of denatured type I collagen (gelatin) which lost its triple helical structure thus indicating that complex formation is not required for cathepsin K-catalyzed degradation of non-collagenous protein substrates. The slightly increased degradation of gelatin in the presence of CSA can be attributed to the stabilizing effect of GAGs on cathepsin K activity during long-time incubation periods as previously reported (Li (2000) supra). Therefore, the collagenolytic activity of cathepsin K only depends on complex formation with CSA but not on cathepsin K stability or interactions between CSA and collagen.

To date, 10 mutations in the cathepsin K gene of pycnodysostosis patients have been described (Gelb et al. (2001) Science 273:1236-1238). With the exception of mutant Y212C, all other mutations characterized to date represent nonsense or missense mutations resulting in unstable proteins or no protein (Hou et al. (1999) J Clin Invest 103:731-738). The carrier of the Y212C mutation is hetero-allelic and has in addition the non-sense mutation, R-241X. Whereas both heterozygous parents do not exhibit the pycnodysostosis phenotype, the double allelic mutations in the child displays the typical disease characteristics such as short stature, skeletal, craniofacial and dental abnormalities.

We have recently shown that mutant Y212C lacked collagenase activity but retained a strong gelatinase activity and significant activities towards synthetic peptide substrates (Hou et al. (1999) supra). We concluded that pycnodysostosis is specifically caused by the deficiency of the collagenolytic activity of cathepsin K and not a priori by the absence of cathepsin K protein and activity.

In the experiments below, it is demonstrated that the Y212C mutant is unable to form a collagenolytically active complex with CSA. Neither at low CSA concentrations (0.2 µg/ml, equal to the concentration of CSA in commercial collagen preparations) nor at high concentrations (1000 µg/ml) any complex formation between Y212C and CSA was observed. In contrast, wild-type cathepsin K formed complexes at both CSA concentrations. The Y212C mutant did not reveal any collagenase activity neither in the presence of or absence of CSA. Thus the lack of complex formation by Y212C explains the inability of this mutant form to hydrolyze native collagen. In contrast, the gelatinase activities of wild-type cathepsin K and mutant protease in the presence of CSA were comparable supporting the hypothesis that complex formation is exclusively required for the collagenase activity of cathepsin K. Complex formation in the presence of CSA is unique for cathepsin K. Closely related cysteine proteases such as cathepsins L, B, and S are unable to form complexes which may explain their inability to cleave in the triple-helical region of interstitial collagens (data not shown).

Examples 15-16 below describe a method for detecting chondroitin4-sulfate (CSA)/Cat K complex formation, and application to a high-through put screening method for identifying agents capable of inhibiting CSA/Cat K complex formation. Example 17 reports the results of mutational studies designed to examine the sites of glycosaminoglycan and cathepsin K interaction.

EXAMPLES

The following examples are put forth so as to provide those of ordinary skill in the art with a complete disclosure and description of how to make and use the collagenolytically active cathepsin K complex, assay, screening, and therapeutic methods of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Hydrolysis of Type I Collagen by Cathepsin K

30 µg of cathepsin K (cat K) were applied to a Superdex 200 column, and eluded with 100 mM sodium acetate buffer, pH 5.5, 1 mM EDTA/DTT, without and with 0.3 M NaCl, cathepsin K degradation fragments eluted as peaks present between 20-28 ml elution volume. Free cathepsin K eluded at Ve 17 ml in the presence of 0.3 M NaCl, whereas it binds to the column in the absence of NaCl. Soluble type I bovine collagen was digested with 800 nM cathepsin K at 28° C., in 100 mM sodium acetate buffer pH 5.5, containing 2.5 mM EDTA/DTT. The reaction was stopped by the addition of 10 µM E-64 after various time periods and the samples were analyzed by 4-20% SDS-Page. The results showed that free cathepsin K displays a weak degradation of type I collagen. Degradation products are likely derived from partially denatured type I collagen. Soluble type I bovine collagen (United States Biochemicals, Cleveland, Ohio) was digested with 800 nM human recombinant cathepsin K in the presence of increasing concentrations of chondroitin 4-sulfate (CSA) at 28° C., in 100 mM sodium acetate buffer, pH 5.5, containing 2.5 mM EDTA/DTT. The reaction was stopped by the addition of 10 µM E-64 after 8 h of incubation and the samples were analyzed by 4-20% SDS-polyacrylamide electrophoresis.

0.2 µg/ml was determined to be the endogenous CSA concentration in commercial type I collagen preparations. The concentration of GAGs dropped to 0.1 µg/ml after depletion of CSA by chondroitinase ABC treatment, accompanied by a strongly reduced ability of cathepsin K to cleave triple helical collagen. At concentrations of CSA at 10 µg/ml and higher, saturation of the complex formation was reached and the cleavage efficacy of type I collagen by cathepsin K/CSA complexes exhibited its maximum. Residual GAGs from commercial type I collagen were removed by treatment with chondroitinase ABC. 100 µl 8 mg/ml collagen (USB, Cleveland, Ohio) in 100 mM sodium acetate buffer, pH 5.5 were incubated with 50 mU chondroitinase ABC (Sigma, St. Louis, Mo.) at 25 C for 4 h. Residual GAG content was determined as followed: 8 mg/mi collagen were heated at 70° C. for 20 min and then incubated with 1 mg/ml pepsin at 25 C, pH 3.7 for 2 h. GAG concentration was measured using the Blyscan glycosaminoglycan assay kit (Biocolor Ltd., Ireland).

Example 2

Cathepsin K/CSA Complex

30 µg of cathepsin K were preincubated with elution buffer containing 0.15% medium molecular size fraction (Ve 58.46 ml) of chondroitin 4-sulfate (CSA) for 20 min, and then applied to a Superdex 200 column. The elution buffer was 100 mM sodium acetate, pH 5.5, 1 mM EDTA/DTT. The CSA/ cathepsin K complex was eluded at Ve of 11 ml.

A mixture of cathepsin K and CSA (30 kD fraction) was fractionated by Superdex 200 gel filtration. In the absence of NaCl, the cathepsin K collagenase activity was associated with a high molecular weight complex of approximately 310 kD.

In the presence of 300 mM NaCl, cathepsin K collagenase activity was eluted from the same mixture as a monomeric protease with an apparent molecular mass of 24 kD. 40 μg of purified recombinant human cathepsin K in the presence of 0.1% CSA were applied to a column and eluted either in the presence or absence of 300 mM NaCl with 100 mM sodium acetate buffer, pH 5.5 containing 1 mM EDTA/ DTT. The protein elution was recorded at $OD_{280}$ nm and fractions were assayed for the hydrolysis of the cathepsin K substrate Z-Leu-Arg-MCA. 50 ng of [$^{125}$I]DCG-04 labeled cathepsin K were preincubated in 100 mM sodium acetate buffer, pH 5.0 containing 0.5 mM EDTA/DTT in the presence or absence of 0.1% of CSA, respectively, for 20 min and then mixed at 37° C. with non-reducing protein loading buffer and preheated agarose gel (37 C; final concentration at 0.4%). The sample was loaded into the well of a 0.5% agarose gel and separated at room temperature at 55 V, 250 mA for 30 min in a running buffer containing 125 mM sodium acetate, pH 5.0,0.5 mM EDTA, 1 mM DTT, 40 mM NaCl, and 0.1% Chaps. The gel was dried and subsequently exposed to an X-ray film. The conditions for lane 3 were modified by the addition of 300 mM NaCl into the agarose gel and running buffer. Table 1 shows the results of collagen hydrolysis of the fluorigenic dipeptide substrate Z-LR-MCA by cathepsin K in the absence and presence of 0.15% CSA and 300 mM NaCl. Activity assays were performed using Z-LR-MCA as substrate in 100 mM sodium acetate buffer, pH 5.5, containing 2.5 mM EDTA/DTT and 0.5 nM recombinant human cathepsin K.

TABLE 1

| Condition | $k_{cat}/K_m$ $(M^{-1}s^{-1}) \times 106$ |
|---|---|
| — | $1.199 \times 10^5$ |
| CSA | $2.404 \times 10^5$ |
| NaCl | $0.982 \times 10^5$ |
| CSA/NaCl | $1.615 \times 10^5$ |

Example 3

Human Cathepsin K Forms Complexes with CSA at a Ratio of 1:1

Increasing amounts of [$^{125}$I]DCG-04 labeled cathepsin K (0 to 1425 pmoles) were separated in a 0.5% agarose gel containing 292 pMol of CSA (30 kD fraction) as described above. After exposure of the dried gel to an X-ray film, the signal of free cathepsin K was densitometrically determined and the amount of cathepsin K in the complex was calculated (cat $K_{complex}$=cat $K_{total}$−cat $K_{free}$). Plotting the ratio cat $K_{complex}$/CSA vs. the cat $K_{total}$ a curve was obtained reaching a plateau at 1 for the cat$K_{complex}$/CSA ratio.

Example 4

Triple-Helical Type I Collagen Degradation by Cathepsin K/CSA

Soluble type I bovine collagen was digested with 800 nM purified recombinant human cathepsin K and gelatin (soluble type I collagen was heated for 20 min at 70 C) with 0.5 nM cathepsin K at 28° C. and 37 C, in 100 mM sodium acetate buffer, pH 5.5, containing 2.5 mM EDTA/DTT. Digestion experiments were carried out in the presence or absence of 300 mM NaCl and 0.15% CSA. The reaction was stopped by the addition of 10 μM E-64 after 8 h of incubation and the samples were analyzed by 4-20% SDS-polyacrylamide electrophoresis.

Example 5

Elution Profile for Cathepsin K Complexes Formed in the Presence of Negatively Charged Polymers 30 μg of cathepsin K were preincubated with elution buffer containing 0.15% low molecular fraction (V3 67.2 ml) of dermatan sulfate (DS) 0.15% 2-15 kD poly-D-Glu, or 0.15% 10 kD dextran sulfate for 20 min, and then applied to a Superdex 200 column. The elution buffer was 100 mM sodium acetate, pH 5.5, containing 1 mM EDTA/DTT. Several cathepsin K complexes were formed. DS/Cat K complex was present at a Ve of 14 ml, poly-D-Glu/Cat K at 14.2 ml, dextran sulfate/Cat K complex at 13.5 ml. These results support the ability of cathepsin K to form complexes with negatively charged linear polymers.

15 μg of cathepsin K were preincubated with running buffer in the presence or the absence of 0.15% high molecular weight fraction (Ve 44.06 ml) of CSA, 0.15% heparin (6 kD), 0.15% keratan sulfate (KS), 0.15% dermatan sulfate (DS), and 0.15% C-6S, respectively, for 20 min. Samples were subsequently mixed with non-reducing protein sample buffer, DNA dye, and melted agarose gel (melted at 37 C; 0.4% final concentration) at 37 C and embedded into a pre-made wells of a 0.5% agarose gel (running conditions: 25° C.; 55 V, 250 mA for 30 min). The gel was stained with toluidine blue for glycosaminoglycans and coomassie blue for protein. The running buffer was 125 mM sodium acetate, pH 5.0,0.5 mM EDTA, 1 mM DTT, 40 mM NaCl, and 0.1% Chaps. The results show that complexes CSA/cathepsin K, heparin/cathepsin K, KS/cathepsin K, DS/Cat K, and C-6S/Cat K, were found in the presence of CSA, heparin, KS, DS, and C-6S, respectively.

Example 6

Gelatin and Type I Collagen Degradation

Gelatin and soluble type I bovine collagen were digested with 800 nM and 1 nM cathepsin K, respectively, at 28° C., 100 mM sodium acetate buffer pH 5.5, 2.5 mM EDTA/DTT, with/without 0.15% CSA, 0.15% dextran sulfate, and 0.15% poly-D-Glu. The reactions were stopped by the addition of 10 μM E-64 and the samples were analyzed by 4-20% SDS-Page. The results show that cathepsin K formed complexes with CSA, dextran sulfate, and poly-D-Glu. The complexes formed with dextran sulfate and poly-D-Glu did not exhibit collagenase activity, but were active against denatured collagen gelatin. All complexes stabilize cathepsin K activity, such that the cumulative gelatinolytic activity (Li et al. (2000) supra) was higher than that of free cathepsin K. Only the CSA/cathepsin K complex displayed activity towards native triple-helical collagen, indicating that the strong collagenolytic activity of the CSA/cathepsin K complex is not caused by increased enzyme stability but is an intrinsic feature of the complex structure.

Example 7

Inhibition of CSA/Cathepsin K Complex Formation by Dextran Sulfate and Poly-D-Glu 15 (g of cathepsin K were preincubated with running buffer in the presence or absence of 0.15% high molecular weight fraction (Ve 44.06 ml) of CSA, 0.15% dextran sulfate (10 kD), and 0.15% poly-D-glu (2-15 kD) for 20 min; 8 (g of free cathepsin K was used as a control. Samples were subsequently mixed with non-reducing protein sample buffer, DNA dye, and melted agarose gel (melted at 37° C.; 0.4% final concentration) at 37° C. and embedded into a pre-made wells of a 0.5% agarose gel (running conditions: 25 oC; 55 V, 250 mA for 30 min). The gel was stained with toluidine blue for glycosaminoglycans and coomassie blue for protein. The running buffer was 125 mM sodium acetate, pH 5.0, 0.5 mM EDTA, 1 mM DTT, 40 mM NaCl, and 0.1% Chaps. In the presence of dextran sulfate or poly-D-Glu, the formation of the CSA/cathepsin K complex was blocked by the competitive formation of dextran sulfate/cathepsin K or poly-D-glu/cathepsin K complexes. This suggests that both dextran sulfate and poly-D-glu bind with a higher affinity to cathepsin K than CSA.

Example 8

Elution Profile for CSA/Cathepsin K Complex in the Presence of 0.15% Dextran Sulfate 30 μg of cathepsin K were preincubated with elution buffer containing 0.15% medium molecular weight fraction (58.46) of CSA and 0.15% dextran sulfate (10 kD) for 20 min, and then applied to a Superdex 200 column. The elution buffer was 100 mM sodium acetate, pH 5.5, 1 mM EDTA/DTT. Instead of the CSA/cathepsin K complex (at Ve of 11 ml) a cathepsin K/dextran sulfate complex was formed (Ve of 13.5 ml). Soluble type I bovine collagen was digested with 800 nM cathepsin K at 28° C., 100 mM sodium acetate buffer pH 5.5, containing 0.15% CSA, 0.15% of dextran sulfate, and 2.5 mM EDTA/DTT. The reaction was stopped by the addition of 10 μM E-64 and the samples were analyzed by 4-20% SDS-Page. The results establish that 0.15% dextrane sulfate prevented the formation of a cathepsin K/CSA complex, and thus prevents the degradation of type I collagen. Dextran sulfates competes with CSA in the complex formation with cathepsin K and forms a complex lacking collagenolytic activity.

Example 9

Elution Profile for CSA/Cathepsin K Complex at 0.15% Poly-D-Glu 30 g of cathepsin K were preincubated with elution buffer containing 0.15% medium molecular weight fraction (Ve 58.46 ml) of CSA and 0.15% poly-D-glu (2-15 kDa) for 20 min, and then applied to a Superdex 200 column. The elution buffer was 100 mM sodium acetate, pH 5.5, 1 mM EDTA/DTT. The CSA/cathepsin K complex (Ve of 11 ml) was not formed, but a cathepsin K/poly-D-glu complex eluted at Ve of 14.2 ml. Soluble type I bovine collagen was digested with 800 nM cathepsin K at 28° C., 100 mM sodium acetate buffer pH 5.5, containing 0.15% CSA, 0.15% poly-D-glu, and 2.5 mM EDTA/DTT. The reaction was stopped by the addition of 10 μM E-64 and the samples were analyzed by 4-20% SDS-Page.

The results established that 0.15% poly-D-glu prevented the formation of a cathepsin K/CSA complex, and thus prevents the degradation of type I collagen. Poly-D-glu competes with CSA in the complex formation with cathepsin K and forms a complex lacking collagenolytic activity.

Example 10

Effect of a 30-mer Oligonucleotide on the Formation of a CSA/Cathepsin K Complex and its Collagenolytic Activity 15 μg of cathepsin K were preincubated with running buffer in the presence or the absence of 0.15% high molecular weight fraction (44.06) of CSA and 0.3% oligonucleotide (11 kDa) for 20 min. Samples were subsequently mixed with non-reducing protein sample buffer, DNA dye, and melted agarose gel (melted at 37 C; 0.4% final concentration) at 37 C and embedded into a pre-made wells of a 0.5% agarose gel (running conditions: 25° C.; 55 V, 250 mA for 30 min). The gel was stained with toluidine blue for glycosaminoglycans and coomassie blue for protein. The running buffer was 125 mM sodium acetate, pH 5.0, 0.5 mM EDTA, 1 mM DTT, 40 mM NaCl, and 0.1% Chaps.

In the presence of both CSA and oligonucleotide, an oligonucleotide/cathepsin K complex was formed instead of the CSA/cathepsin K complex. Soluble type I bovine collagen was digested with 800 nM cathepsin K at 28° C., 100 mM sodium acetate buffer pH 5.5, containing 0.15% CSA, 0.3% of oligonucleotide, and 2.5 mM EDTA/DTT. The reaction was stopped by the addition of 10 μM E-64 and the samples were analyzed by 4-20% SDS-Page. 0.3% of a 30-mer oligonucleotide prevented the formation of a cathepsin K/CSA complex, and thus prevents the degradation of type I collagen. The oligomer-nucleotide competed with CSA in the complex formation with cathepsin K and forms a complex lacking collagenolytic activity.

Example 11

Effect of CSA Disaccharide on Free Cathepsin K and CSA/Cathepsin K Complex Formation 30 μg of cathepsin K were preincubated with elution buffer containing 0.15% CSA disaccharide without or with 0.15% medium molecular weight fraction (Ve 58.46 ml) of CSA for 20 min, and then applied to a Superdex 200 column. The elution buffer was 100 mM sodium acetate, pH 5.5, 1 mM EDTA/DTT. Soluble type I bovine collagen was digested with 800 nM cathepsin K at 28° C., 100 mM sodium acetate buffer pH 5.5, containing 0.15% CSA, 0.15% CSA disaccharide, and 2.5 mM EDTA/DTT. The reaction was stopped by the addition of 10 μM E-64 and the samples were analyzed by 4-20% SDS-Page.

CSA disaccharides were unable to generate high-molecular complexes with cathepsin K and did not interfere with complex formation in the presence CSA. Thus, the collagenolytic activity of the CSA/cathepsin K complex was identical in the presence of CSA disaccharide. This suggests that chondroitin disaccharide-4S does not bind with cathepsin K, and neither affected the CSA/cathepsin K complex formation or the collagenolytic activity of the complex.

Example 12

Effect of Dextran on Free Cathepsin K and CSA/Cathepsin K Complex Formation

30 μg of cathepsin K were preincubated with elution buffer containing 0.15% dextran (18 kD) without or with 0.15% medium molecular weight fraction (58.46) of CSA for 20 min, and then applied to a Superdex 200 column. The elution buffer was 100 mM sodium acetate, pH 5.5, 1 mM EDTA/DTT. The results showed that dextran did not form a high molecular weight complex with cathepsin K. Further, the formation of the CSA/cathepsin K complex (Ve of 11 ml) was not affected by dextran. Soluble type I bovine collagen was digested with 800 nM cathepsin K at 28° C., 100 mM sodium acetate buffer pH 5.5, containing 0.15% dextran and 2.5 mM EDTA/DTT with/without 0.15% CSA. The reaction was stopped by the addition of 10 µM E-64 and the samples were analyzed by 4-20% SDS-Page.

Dextran, a neutral polysaccharide was unable to generate high-molecular complexes with cathepsin K and did not interfere with the complex formation in the presence CSA. Thus, the collagenolytic activity of the CSA/cathepsin K complex was identical in the presence of dextran.

Example 13

Lack of Complex Formation for Human Cathepsins L, B, and S 50 ng of [$^{125}$I]DCG-04 labeled cathepsin K Y212C, Cat L, Cat B, and Cat S were preincubated with running buffer in the presence or the absence of 0.1% of CSA, respectively, for 20 min, and then at 37° C. mixed the samples with non-denature protein sample buffer, DNA dye, and 37° C. agarose gel (final concentration at 0.4%), and submitted to 0.5% agarose gel in running buffer. The gel was run at about 25° C. 55 V, 250 mA for 30 min, then dried and developed the radio signal on a film. The running buffer was 125 mM sodium acetate, pH 5.0, 0.5 mM EDTA, 1 mM DTT, 40 mM NaCl, and 0.1% chaps. Only cathepsin K formed a stable complex in the presence of CSA.

Example 14

Lack of Complex Formation with Pycnodysostosis-Causing Cathepsin K Mutant, Y212C

[$^{125}$I]DCG-04 labeled wild-type cathepsin K and mutant Y212C were separated in the presence or absence of 0.2 µg/ml and 1000 µg/ml CSA, respectively, in a 0.5% agarose gel as described above. Y212C was unable to form a complex with CSA at either low or high CSA concentrations. Type I collagen was incubated with 800 nM of recombinant Y212C and 800 nM wild-type cathepsin K in the absence or presence of 0.15% CSA and analyzed by SDS-polyacrylamide electrophoresis. The result showed that Y212C was not able to hydrolyze type I collagen. Gelatin hydrolysis was performed in the presence of 1 nM Y212C, 0.15% CSA at 37 C for 8 h. The results showed that Y212C exhibited gelatinase activity.

Example 15

Method for Detection of CSA/Cat K Complex Formation and Application for High-Through Put Screening (HTS) of Complex Formation Inhibitors 20 mg cyanogen bromide (CNBr) dissolved in 200 µl deionized water were added to 1 ml of 30 mg/ml chondroitin 4-sulfate (CSA). The pH was adjusted to pH 11 by addition of 5 M NaOH. Activated CSA is applied to a PD-10 column and eluded with 200 mM sodium borate buffer, pH 8.0. CSA fractions were directly dropped into 400 µl of 10 mg/ml fluoresceinamine in 200 mM sodium borate buffer, pH 8.0. The mixture was kept overnight at 4° C. for the coupling reaction. Subsequently, the mixture was concentrated to 1 ml using a SpeedVac concentrator and purified on a PD-10 column and eluded by 50 mM sodium acetate buffer, pH 5.5. Fluoresceinamine-labeled CSA (FL-CSA) fractions were collected and their concentration was determined using the Blyscan glycosaminoglycan assay kit (Biocolor Ltd., Newtown Abbey, Northern Ireland).

Fluoresceinamine-labeled CSA/Cat K complex formation was detected in a Perkin-Elmer fluorimeter at excitation and emission wavelengths of 300 nm and 604 nm, respectively. Cat K at a final concentration of 120 nM was added to 1 ml 100 mM sodium acetate buffer, pH 5.5 containing 2 mM EDTA/DTT using 2 milliliter cuvettes. The fluorescence signal for the protein alone is close to zero. After the addition of fluoresceinamine-labeled CSA at a final concentration of 0.6 µg/ml, the fluorescence signal increased reaching a saturation maximum after 5-10 min. This is expected to reflect the generation of the catK/labeled CSA complex. Like the protein alone, fluoresceinamine-labeled CSA does not have a fluorescence signal by itself at the wavelengths used for the assay. After the addition of complex formation inhibitors, the fluorescence signal dropped to zero (FIG. 1). This assay allows the simple and convenient screening of compounds capable to interfere with complex formation. If the fluorescence signal significantly decreases after adding a certain concentration of a compound (e.g., 6 µg/ml of dextran sulfate) this compound can be selected as a potential inhibitor of CatK/CSA complex formation.

The following test compounds have been demonstrated to decrease the fluorescence signal: dextran sulfate, dermatan sulfate, heparan sulfate, poly-glutamic acid, poly-aspartic acid (results not shown). In contrast, dextran, poly-lysine, poly-alanine, and chondroitin disaccharide-4S did not show any effect on the fluorescence signal. All compounds decreasing the fluorescence signal have been independently demonstrated to form a complex with catK as shown by the agarose gel electrophoretic mobility shift assay and gel filtration and to block or significantly decrease the collagenolytic activity of the catK/CSA complex. Compounds not affecting the fluorescence signal did not reveal a gel mobility shift or a decrease of the collagenolytic activity of the protease complex.

Example 16

High Throughput Assay for Screening of Complex Formation Inhibitors

The single cuvette assay described above is translated into a 96 well format allowing the automation of the screening process. The following protocol is followed: 1 positive control (100 nM Cat K, 0.5 µg/ml FL-CSA, and 5 µg/ml of dextrane sulfate), 1 negative control (100 nM Cat K+0.5 µg/ml Fl-CSA), and two concentrations of the test compound (100 nM Cat K+0.5 µg/ml and 10 µg/ml test compound) in separate wells with 200 µl of 100 mM sodium acetate buffer, pH 5.5 containing 2 mM EDTA/DTT. The samples are mixed using the automixer and the fluorescence signal is monitored in a microplate fluorescence reader (Gemini XS) using the excitation and emission wavelengths of 300 nm and 604 nm, respectively. If the signal is significantly decreased in a testing well comparing to the negative control, the compound can be selected for further evaluation of its complex formation capabilities.

Example 17

Identification of Potential Binding Sites for Chondroitin Sulfate on Cathepsin K Polypeptide Using protein alignment and structure modeling strategies, two potential sites of glycosaminoglycan and cathepsin K interactions were identified and analyzed by site-directed mutagenesis. The following basic amino acid residues (lysines (K) and arginines (R)) were found to be unique for cathepsin K and located in two clusters on the backside of the protease (opposing the active site cleft): K77, R79, K103, K106, R108, R111, K122, R127 (cluster 1); R8, K9, K10, (cluster 2). The triple basic cluster (R8,K9, K10) fits the basic amino acid residue motif known to bind sulfate glycosaminoglycans.

The mutant proteins were generated to characterize cluster 1:K77A, R79A (mutant 1), K103, K106A, R108A, R111A, (mutant 2), K77A, R79A, K103, K106A, R108A,R111A (mutant 3), K77A, R79A, K103, K106A, R108A,R111A, K122A, R127A (mutant 4). Mutant proteins were expressed in *Pichia pastoris* and the activity of the protein was determined towards two synthetic peptide substrates, gelatin and type I native collagen. Wild-type cathepsin K and mutant proteins were incubated for 8 h at 28 C at a concentration of 800 nM with type I collagen (0.4 mg/ml) in sodium acetate buffer, pH 5.5 containing 2.5 mM DTT/EDTA in the presence of 0.15% CSA. The cleavage products were separated by SDS polyacrylamide electrophoresis using 4-20% Tris Glycine gels. Wild-type cathepsin K and mutant 1 reveal a complete degradation of type I collagen whereas mutants 2, 3, 4 and 5 are strongly inhibited.

Mutant proteins and wild type displayed only minor or no differences in their activity towards the synthetic peptide substrates and gelatin. In contrast a significant inhibition of their collagenolytic activity was observed for mutants 2, 3 and 4. The degree of inhibition for all three mutants was comparable suggesting that the residues important for the collagenolytic activity are located in residues K103, K106A, R108A, R111A (mutant 2). Mutant 1 (K77A, R79A) did not reveal an inhibition, thus excluding both sites. Mutants 3 and 4 are cumulative mutants of mutants 1, 2 and mutant 3 plus residues K122 and R127. Results obtained from gel-mobility assays did not reveal prevention of complex formation, however, suggesting that either cluster 1 or 2 are individually sufficient for complex formation. However, the utilization of only one of the binding motifs or alternative binding motifs appears to be insufficient to maintain the overall structure of the collagenolytically active cathepsinK complex with CSA, thus preventing or significantly reducing its collagenolytic activity. These complexes are designated as "non-productive complexes" similar to the collagenolytically inactive complexes of cathepsin K observed in the presence of dermatan or dextran sulfate.

A preliminary crystal structure of cathepsin K in the presence of CSA revealed interactions with the predicted triple basic motif (R8, K9, K10) in cluster 2. The structure did not show interactions with cluster 1 and furthermore revealed a ratio of 1:n (n+10 or more depending on the length of CSA used in the crystallization experiment) between CSA and cathepsin K. This ratio is in contrast to the 1:1 ratio obtained for catK/CSA complexes in solution which as collagenolytically active. It was assumed that the crystal structure is a crystallization artifact which nevertheless may reveal partial interactions between the cathepsin K protein and CSA. In particular, residue K9 showed close contacts with a sulfate group of CSA. Replacing this residue with glutamic acid (mutant 5 (K9E; Glu is present in cathepsin L at this position and cathepsin L does not form complexes with CSA) resulted in a protein which was fully active towards synthetic peptide substrates and gelatin but significantly reduced its activity towards type I collagen (results not shown). Similar to the mutations in cluster 1, the cluster 2 mutant still revealed complex formation in the presence of CSA in the mobility shift assay indicating again that disruption of interaction within the individual clusters is insufficient for a total abolition of complex formation.

The present invention is not to be limited in terms of the particular embodiments described in this application, which are intended as single illustrations of individual aspects of the invention. Functionally equivalent methods and apparatus within the scope of the invention, in addition to those enumerated herein, will be apparent to those skilled in the art from the foregoing description and accompanying drawings. Such modifications and variations are intended to fall within the scope of the appended claims.

I claim:

1. A purified collagenolytically active oligomeric cathepsin K complex comprising at least two cathepsin K peptides and a 1:1 ratio of glycosaminoglycan molecules, wherein the complex has collagenolytic activity to degrade Type I and II collagen substrate.

2. The purified cathepsin K complex of claim 1, comprising 2-10 cathepsin K peptides and 2-10 glycosaminoglycan molecules in said complexed at a 1:1 ratio, wherein complex formation is inhibited by high salt.

3. The purified cathepsin K complex of claim 1, wherein the glycosaminoglycan is selected from the group consisting of chondroitin sulfate and keratan sulfate.

4. A pharmaceutical composition comprising the cathepsin K complex of claim 1.

5. A kit comprising the pharmaceutical composition of claim 4.

6. A method of inhibiting the collagenolytic activity of cathepsin K in a mammal comprising administering to said mammal an effective amount of a reagent that inhibits the collagenolytic activity of cathepsin K by disrupting the collagenolytically active oligomeric cathepsin K complex comprising at least two cathepsin K peptides and a 1:1 ratio of glycosaminoglycan molecules or by interfering with the formation of a collagenolytically active oligomeric complex of cathepsin K peptides and glycosaminoglycans, wherein the reagent specifically inhibits the collagenolytic activity and not the gelatinase activity of cathepsin K, and wherein the reagent is selected from one or more of dextran sulfate, dermatan sulfate, heparan sulfate, poly-glutamic acid, and poly-aspartic acid.

7. The method of claim 6 wherein the glycosaminoglycan is selected from the group consisting of chondroitin sulfate and keratan sulfate.

8. The method of claim 6 wherein the reagent is a glycosaminoglycan that forms a collagenolytically inactive complex with cathepsin K and is selected from dextran sulfate and dermatan sulfate.

9. The method of claim 6 wherein the mammal has excessive degradation of extracellular bone and/or cartilage matrix and collagenolytic activity in bone and/or cartilage matrix is inhibited by administration of the reagent.

* * * * *